US00PP26867P2

(12) United States Plant Patent
van der Zwet

(10) Patent No.: US PP26,867 P2
(45) Date of Patent: Jun. 21, 2016

(54) ***CAMPANULA* PLANT NAMED 'CHICO MERANO'**

(50) Latin Name: *Campanula glomerata*
Varietal Denomination: Chico Merano

(71) Applicant: Alexius Joannes Joseph van der Zwet, Oude-Wetering (NL)

(72) Inventor: Alexius Joannes Joseph van der Zwet, Oude-Wetering (NL)

( * ) Notice: Subject to any disclaimer, the term of this patent is extended or adjusted under 35 U.S.C. 154(b) by 1 day.

(21) Appl. No.: 14/121,886

(22) Filed: Oct. 31, 2014

(51) Int. Cl.
*A01H 5/02* (2006.01)

(52) U.S. Cl.
USPC ..... Plt./414

(58) Field of Classification Search
USPC ..... Plt./414
CPC ..... A01H 5/02
See application file for complete search history.

*Primary Examiner* — Kent L Bell
(74) *Attorney, Agent, or Firm* — C. A. Whealy

(57) ABSTRACT

A new and distinct *Campanula* plant named 'Chico Merano', characterized by its compact and broadly upright plant habit; basal branching habit; freely flowering habit; purple violet-colored flowers; and long flowering period.

2 Drawing Sheets

Botanical designation: *Campanula glomerata.*
Cultivar denomination: 'CHICO MERANO'.

BACKGROUND OF THE INVENTION

The present invention relates to a new and distinct *Campanula* plant, botanically known as *Campanula glomerata* and hereinafter referred to by the cultivar name 'Chico Merano'.

The new *Campanula* plant is a product of a planned breeding program conducted by the Inventor in Oude-Wetering, The Netherlands. The objective of the breeding program is to create new freely-flowering *Campanula* plants that flower for a long period of time.

The new *Campanula* plant originated from an open-pollination during the summer of 2006 of an unnamed selection of *Campanula glomerata,* not patented, as the female, or seed, parent with an unknown selection of *Campanula glomerata,* as the male, or pollen, parent. The new *Campanula* plant was discovered and selected by the Inventor as a single flowering plant from within the progeny of the stated open-pollination grown in a controlled environment in Oude-Wetering, The Netherlands during the summer of 2007.

Asexual reproduction of the new *Campanula* plant by divisions a controlled environment in Oude-Wetering, The Netherlands, since August, 2009, has shown that the unique features of the new *Campanula* plant are stable and reproduced true to type in successive generations.

SUMMARY OF THE INVENTION

Plants of the new *Campanula* plant have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Chico Merano'. These characteristics in combination distinguish 'Chico Merano' as a new and distinct *Campanula* plant:

1. Compact and broadly upright plant habit.
2. Basal branching habit.
3. Freely flowering habit.
4. Purple violet-colored flowers.
5. Long flowering period.

Plants of the new *Campanula* differ from plants of the female parent selection primarily in plant size and flower color.

Plants of the new *Campanula* can be compared to plants of *Campanula* 'Blue Ocean', not patented. In side-by-side comparisons conducted by the Inventor in Oude-Wetering, The Netherlands, plants of the new *Campanula* differed primarily from plants of 'Blue Ocean' in the following characteristics:

1. Plants of the new *Campanula* were more compact than plants of 'Blue Ocean'.
2. Plants of the new *Campanula* had stronger stems than plants of 'Blue Ocean'.
3. Plants of the new *Campanula* were more freely branching than plants of 'Blue Ocean'.
4. Plants of the new *Campanula* had darker-colored flowers than plants of 'Blue Ocean'.

Plants of the new *Campanula* can also be compared to plants of *Campanula* 'Blue Bird', not patented. In side-by-side comparisons conducted by the Inventor in Oude-Wetering, The Netherlands, plants of the new *Campanula* differed primarily from plants of 'Blue Bird' in the following characteristics:

1. Plants of the new *Campanula* were more compact than plants of 'Blue Bird'.
2. Plants of the new *Campanula* had stronger stems than plants of 'Blue Bird'.
3. Plants of the new *Campanula* were more freely branching than plants of 'Blue Bird'.
4. Plants of the new *Campanula* had darker-colored flowers than plants of 'Blue Bird'.

BRIEF DESCRIPTION OF THE PHOTOGRAPHS

The accompanying colored photographs illustrate the overall appearance of the new *Campanula* plant showing the colors as true as it is reasonably possible to obtain in colored reproductions of this type. Colors in the photographs may differ slightly from the color values cited in the detailed botanical description which accurately describe the actual colors of the new *Campanula* plant.

The photograph on the first sheet comprises a side perspective view of a typical flowering plant of 'Chico Merano' grown in a container.

The photograph on the second sheet is a close-up view of a flowering stem of 'Chico Merano'.

DETAILED BOTANICAL DESCRIPTION

Plants used for the aforementioned photographs and following description were grown in 29-cm containers during the spring and early summer in a glass-covered greenhouse in Oude-Wetering, The Netherlands and under cultural practices typical of commercial *Campanula* production. During the production of the plants, day temperatures ranged from 15° C. to 25° C. and night temperatures ranged from 5° C. to 16° C. Plants were two years old when the photographs and description were taken. In the following description, color references are made to The Royal Horticultural Society Colour Chart, 2007 Edition, except where general terms of ordinary dictionary significance are used.

Botanical classification: *Campanula glomerata* 'Chico Merano'.

Parentage:

*Female parent*.—Unnamed selection of *Campanula glomerata,* not patented.

*Male parent*.—Unknown selection of *Campanula glomerata,* not patented.

Propagation:

*Type*.—By divisions.

*Root description*.—Medium in thickness, fibrous; white in color.

*Rooting habit*.—Freely branching; medium density.

Plant description:

*Plant and growth habit*.—Herbaceous perennial; compact and broadly upright plant form; inverted triangle; low vigor to moderately vigorous growth habit; campanulate flowers arranged in terminal and axillary clusters.

*Plant height*.—About 37.4 cm.

*Plant width*.—About 51.5 cm.

*Branch description*.—Branching habit: Freely branching habit with about five primary branches developing per plant. Length: About 35.3 cm. Diameter: About 7 mm. Internode length: About 1.4 cm. Strength: Strong. Aspect: Upright to about 30° from vertical. Texture: Densely pubescent. Color: Close to 144A to 144B strongly tinged with close to 184A to 184D.

Leaf description:

*Arrangement*.—Alternate, simple.

*Length*.—About 8.6 cm.

*Width*.—About 3.9 cm.

*Shape*.—Ovate.

*Apex*.—Acute.

*Base*.—Truncate or cordate.

*Margin*.—Finely serrate.

*Texture, upper and lower surfaces*.—Moderately rugose, rough; moderately pubescent.

*Venation pattern*.—Pinnate.

*Color*.—Developing leaves, upper surface: Close to between 143A and 144A. Developing leaves, lower surface: Close to 143C. Fully expanded leaves, upper surface: Close to 137B; venation, close to 144D. Fully expanded leaves, lower surface: Close to 138B; venation, close to 144B.

*Petioles*.—Stem leaves are sessile; basal leaves are petiolate. Length: About 13.3 cm. Diameter: About 3 mm by 3 mm. Color, upper and lower surfaces: Close to 144B; proximally tinged with close to 182B to 182C; margins, close to 144A.

Flower description:

*Flower arrangement and flowering habit*.—Single campanulate flowers arranged in terminal and axillary clusters; flowers face mostly upright to slightly outwardly; freely flowering habit with about 25 flowers developing in terminal clusters and about six flowers developing in axillary clusters.

*Natural flowering season*.—Plants begin flowering about nine months after planting; relatively long flowering period, plants flower continuously from mid-June to early August in The Netherlands.

*Flower longevity on the plant*.—About ten days; flowers persistent.

*Fragrance*.—None detected.

*Flower buds*.—Length: About 2.5 cm. Diameter: About 1.4 cm. Shape: Narrowly oblong. Color: Close to between N77A and N77B.

*Flower cluster height*.—About 5.3 cm.

*Flower cluster diameter*.—About 8.5 cm.

*Flower diameter*.—About 3.6 cm.

*Flower depth* (*height*).—About 3.5 cm.

*Petals*.—Arrangement: Five in a single whorl; fused. Length: About 3.4 cm. Width: About 8 mm. Shape: Narrowly oblong. Apex: Acute. Margin: Entire. Texture, upper and lower surfaces: Smooth, glabrous. Color: When opening and fully opened, upper surface: Close to N82A; color does not fade with development. When opened and fully opened, lower surface: Close to between N82A and 83C; color does not fade with development.

*Sepals*.—Arrangement: Five in a single whorl; fused. Length: About 1.4 cm. Width: About 3 mm. Shape: Lanceolate. Apex: Narrowly acute. Margin: Entire. Texture, upper and lower surfaces: Densely pubescent. Color: When opening and fully opened, upper surface: Close to 137C to 137D; towards the apex, close to 147A. When opening and fully opened, lower surface: Close to 137D; towards the apex, close to 147A.

*Peduncles*.—Length: About 6 mm. Diameter: About 5 mm. Aspect, flowers in terminal clusters: Mostly upright. Aspect, flowers in axillary clusters: About 30° from branch. Strength: Strong. Texture: Smooth, glabrous. Color: Close to 144A to 144B strongly tinged with close to 184A to 184D.

*Reproductive organs*.—Stamens: Quantity per flower: Six. Filament length: About 3 mm. Filament color: Close to NN155C. Anther shape: Lanceolate. Anther length: About 6 mm. Anther color: Close to 11A. Pollen amount: Scarce. Pollen color: Close to 4D. Pistils: Quantity per flower: One. Pistil length: About 1.7 cm. Stigma shape: Three-parted, decurrent. Stigma color: Close to 182B. Style length: About 1.5 cm. Style color: Close to N82D. Ovary color: Close to 145B to 145C.

*Seeds and fruits*.—Seed and fruit production has not been observed on plants of the new *Campanula*.

Disease & pest resistance: Plants of the new *Campanula* have not been noted to be resistant to pathogens and pests common to *Campanula* plants.

Garden performance: Plants of the new *Campanula* have exhibited good tolerance to rain and wind, to tolerate high temperatures about 35° C. and to be hardy to USDA Hardiness Zones 3.

It is claimed:

1. A new and distinct *Campanula* plant named 'Chico Merano' as illustrated and described.

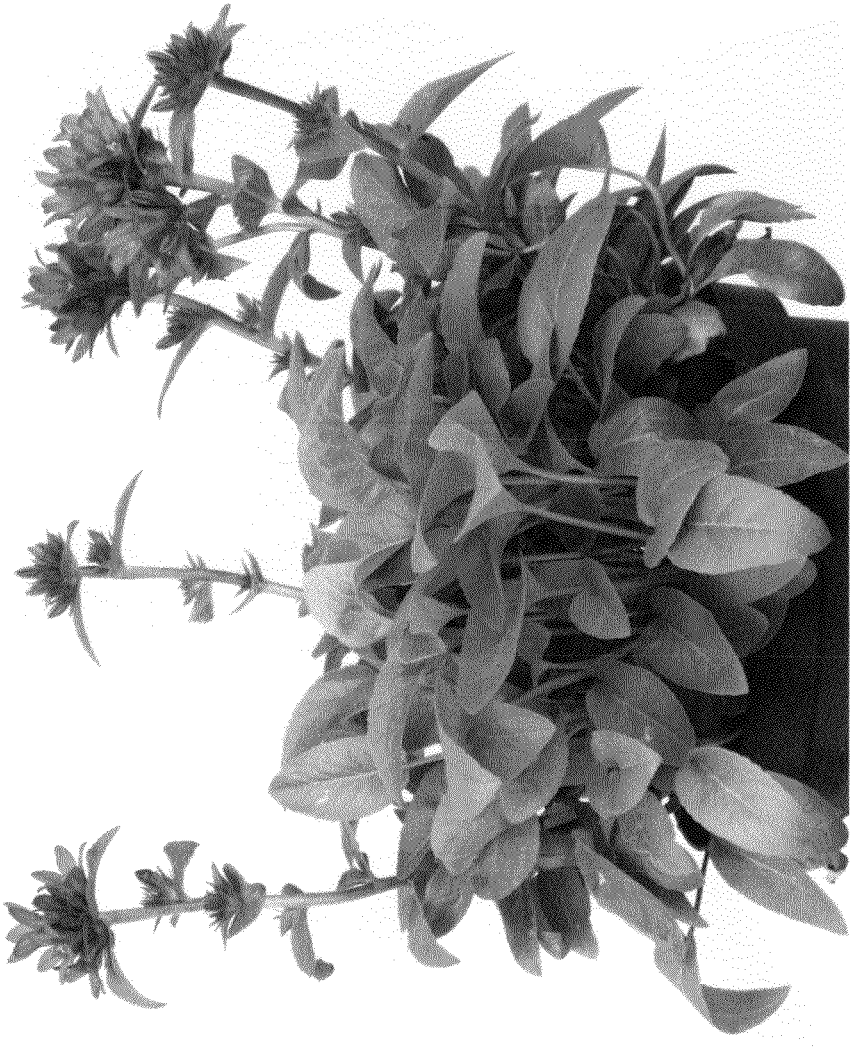

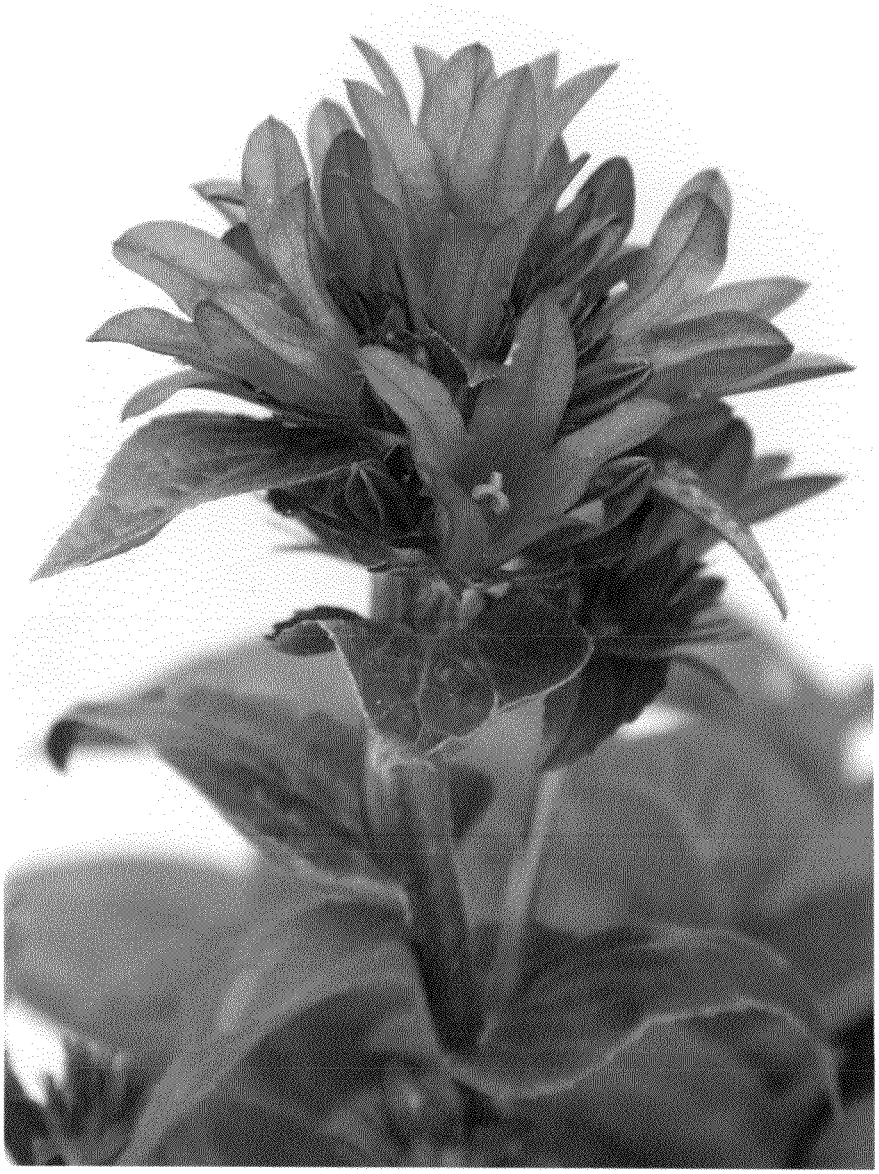

* * * * *